United States Patent [19]
Georger, Jr. et al.

[11] Patent Number: 5,510,628
[45] Date of Patent: Apr. 23, 1996

[54] DEEP ULTRAVIOLET PHOTOLITHOGRAPHICALLY DEFINED ULTRA-THIN FILMS FOR SELECTIVE CELL ADHESION AND OUTGROWTH AND METHOD OF MANUFACTURING THE SAME AND DEVICES CONTAINING THE SAME

[75] Inventors: Jacque H. Georger, Jr., Springfield; David A. Stenger, Reston, both of Va.; Thomas L. Fare, Washington, D.C.

[73] Assignee: Geo-Centers, Inc., Newton Centre, Mass.

[21] Appl. No.: 206,147

[22] Filed: Mar. 7, 1994

Related U.S. Application Data

[60] Division of Ser. No. 598,194, Oct. 16, 1990, Pat. No. 5,324,591, which is a continuation-in-part of Ser. No. 182,123, Apr. 14, 1988, Pat. No. 5,079,600, which is a continuation-in-part of Ser. No. 22,439, Mar. 6, 1987, Pat. No. 5,077,085.

[51] Int. Cl.$^6$ .............................. H01L 27/12; B05D 5/12
[52] U.S. Cl. .............................. 257/32; 257/37; 427/98
[58] Field of Search .................. 257/32, 37; 427/54.1, 427/98

[56] References Cited

U.S. PATENT DOCUMENTS

| 3,884,704 | 5/1975 | Bantell | 427/98 |
|---|---|---|---|
| 4,199,649 | 4/1980 | Yundt | 427/96 |
| 4,539,061 | 9/1985 | Sagiv | 427/407.1 |
| 4,587,203 | 5/1986 | Brault | 427/54.1 |
| 4,661,372 | 4/1987 | Mance | 357/4 |
| 5,079,600 | 1/1992 | Schnur et al. | 357/4 |

*Primary Examiner*—Peter A. Nelson
*Attorney, Agent, or Firm*—Oblon, Spivak, McClelland, Maier & Neustadt

[57] ABSTRACT

Patterned surfaces for the selective adhesion and outgrowth of cells are useful in cell culture devices, prosthetic implants, and cell-based microsensors. Such surfaces may be prepared by a deep ultraviolet photolithographic technique.

23 Claims, 7 Drawing Sheets

DEEP ULTRAVIOLET PHOTOLITHOGRAPHICALLY DEFINED ULTRA-THIN FILMS FOR SELECTIVE CELL ADHESION AND OUTGROWTH AND METHOD OF MANUFACTURING THE SAME AND DEVICES CONTAINING THE SAME

U.S. GOVERNMENT RIGHTS IN THE INVENTION

This invention was made jointly by two employees of the Naval Research Laboratory, Washington, D.C. and one employee of Geo-Centers, Inc. The one Geo-Centers employee, at the time the invention was made, was in the performance of work under Naval Research Laboratory contract N00014-86-C-2540. The United States of America has certain rights in the invention arising out of that contract, including a nonexclusive, nontransferable, irrevocable, paid-up license to practice the invention or have it practiced for or on behalf of the United States throughout the world. The United States of America may also have rights in the invention derived from the two employees of the Naval Research Laboratory who are joint inventors of this invention.

This is a division of application Ser. No. 07/598,194, filed on Oct. 16, 1990, now Pat. No. 5,329,591, which is a Continuation-In-Part of application Ser. No. 07/182,123, now U.S. Pat. No. 5,079,600, filed on Apr. 14, 1988, which is a Continuation-In-Part of application Ser. No. 07/022,439, filed on Mar. 6, 1987, and now Pat. No. 5,077,085.

BACKGROUND OF THE INVENTION

1. Field of the Invention

The present invention relates to patterned ultra-thin films (UTF) for the selective adhesion and outgrowth of cells and a method for producing such films. The present invention also relates to devices which contain such ultra-thin films, such as body implants or prosthetics, cell culture apparatus, and cell based sensors.

2. Discussion of the Background

It is well known that the morphological and functional development of adherent types of biological cells is critically dependent on, among other factors, the physical and geometrical properties of the underlying substrate. The effects of the substrate adhesivity, in particular, on these developmental processes have been vigorously investigated during recent years. However, substrates which are either unmodified, or completely remodified with only a single type of substrate coating have been used almost exclusively.

In many situations, the ability to influence and/or monitor a variety of intra- and intercellular processes using substrate geometry requires that the adhesive properties of that substrate be defined with a spatial resolution of cellular or subcellular dimensions (10 μm to less than 1 μm). For example, substrate patterns designed to spatially direct the adhesion and outgrowth of cells on the surfaces of sensor devices, prosthetic implants, and tissue repair templates are desired.

Several methods have been devised which might conceivably be used for the fabrication of substrate patterns used in the above-mentioned applications. The earliest reported methods rely on definition of a selectively adhesive substrate pattern by mechanically removing cell-repulsive phospholipid films or evaporated gold from cell-adhesive glass substrates (Ivanova et al, *Nature*, Vol. 242, p. 200 (1973)); and Cooper et al, *Exp. Cell Res.*, Vol. 103, p. 435, (1976)) or by masked evaporation of cell-adhesive silicon monoxide onto polystyrene surfaces (Albrecht-Buehler, *J. Cell Biol.*, Vol. 80, p. 53 (1980)). However, these methods suffer from drawbacks due to the instability of phospholipid films, the difficulty associated with the physical removal of thin coatings, and the limited number of materials which may be deposited by evaporation. More importantly, these methods are limited by their reliance on the native adhesive properties of unmodified regions of the substrates.

Other methods have been introduced to create substrate patterns which are based on molecular recognition between the cell surface and bulk protein films on the substrate. Hammarback et al. have shown that the outgrowth of dissociated chick embryo dorsal root ganglion neurons occurs on substrates which are defined using patterned UV irradiation to selectively denature cell-adhesive laminin films (Hammarback et al, *Jour. Neurosci. Res.*, Vol. 13, p. 213 (1985)). An alternative method is to adhere neurons to laminin which has been selectively adhered to regions of albumin films which have become crosslinked by patterned UV exposure (Hammarback et al, *Devel. Biol.*, Vol. 117, p. 655 (1986)). Although the development of most neurites is noticeably affected by the substrate patterns, a significant percentage (10–20%) of the plated cells initially adhere to and at least partially develop on the UV-denatured laminin regions.

Recently, pure UTFs of cell adhesion peptides (Arg-Gly-Asp and Try-Ile-Gly-Ser-Arg) have been formed by covalent linkage to silane-modified glass surfaces (Massia et al, *Anal. Biochem.*, vol. 187, p. 292 (1990)), providing a much better defined system for cell adhesion. In this case, the adhesion is affected by known chemical functionalities which are present on the surface as a monolayer.

Silane films are anchored to the silicon substrate by chemical and physical adsorption, which may involve siloxane (Si-O-Si) bridges or van der Waals forces. Any substrate having a terminal ionizable hydroxyl group at the surface can provide an anchorage for the silane film. This procedure of using self-assembling films involves covalent bond formation between the monolayer and the substrate whereby the film adheres to the substrate more strongly than physisorbed Langmuir-Blodgett films.

The potential for producing high resolution patterns of silane-coupled UTFs has been demonstrated by Kleinfield et al., *Jour. Neurosci.*, vol. 8, p. 4098 (1988). In this method, a conventional photoresist is photolithographically patterned and used to mask silicon and quartz substrate regions. The cell adhesivity of the exposed substrate is reduced by formation of a patterned UTF of covalently attached n-tetradecane. Removal of the photoresist and subsequent recoating of the previously masked regions with EDA produces high resolution (10 μm line-space pairings) regions having completely different cell adhesivities.

Photoresist-defined UTFs have been used to very effectively to define both the initial adhesion and outgrowth of a heterogeneous mixture of cells (various types of glial cells and neurons) from the fetal rat cerebellum (Klienfeld et al, *Jour. Neurosci.*, Vol. 8, p. 4098, (1988)). The photoresist-based UTF patterning process is important because it demonstrates that the entire substrate surface may be modified in the same molecular plane with high resolution, alternating UTF films having a desired two-dimensional architecture. However, the technique has significant drawbacks, the most notable of which is the number of steps required for fabrication due to the adhesion, polymerization, development, and stripping of the photoresist (18 steps are reported in Klienfeld et al, *Jour. Neurosci.*, Vol. 8, p. 4098 (1988)).

Another method has been developed recently for the formation of orthogonal UTFs, (Laibinis et al, *Science*, Vol. 245, p. 845 (1989)). In this method, high resolution monolayer patterns are formed by the selective adsorption of alkanethiols on gold and alkane carboxylic acids on alumina. Selective cell adhesion has not been demonstrated on substrates prepared by this method. However, a large number of chemical functionalities should be compatible with this method, making it a possible fabrication technique for high resolution cell adhesive patterning. A significant limitation of the technique is that only hydrophobic UTF films may be formed on alumina (Laibinis et al, *Science*, Vol. 245, p. 845 (1989)).

U.S. Pat. No. 4,832,759 describes the use of "surface discontinuities" to at least partially define cell adhesion in zones having a width of between 0.2 and 20 µm. U.S. Pat. Nos. 4,591,570 and 4,011,308 describe the use of patterns or arrays of antibody-coated spots for specific immunoabsorption of cells to optically-sensitive surfaces. U.S. Pat. No. 4,562,157 describes the photo-induced activation of adhered chemical species so that chemical functionalities and proteins may be covalently attached to "BIOCHEMFET" devices. However, this work does not address the problem of nonspecific absorption of proteins.

At least one biosensor has been developed which optically measures the metabolic activity of immobilized cells (Parce et al, *Science*, Vol. 246, p. 243 (1989)). However, groups of cells, not individual cells, are "immobilized" by gravitational sedimentation into micromachined silicon wells.

U.S. patent applications Ser. Nos. 07/022,439 filed Mar. 6, 1987 and 07/182,123 filed Apr. 14, 1988 disclose a method for preparing high resolution patterns of metals on solid substrates, by irradiation of an adherent thin film with deep ultraviolet (DUV) irradiation. However, there is no suggestion of patterned substrates for the selective adhesion and outgrowth of cells.

Thus, there remains a need for patterned ultra-thin films for the selective adhesion and outgrowth of cells which are free of the above-mentioned drawbacks. There also remains a need for a method producing such films and devices, such as body implants, cell culture apparatus, cell sensors, and neural prostheses, which utilize such ultra-thin films.

SUMMARY OF THE INVENTION

Accordingly, it is one object of the present invention to provide novel patterned ultra-thin films for the selective adhesion and outgrowth of cells.

It is another object of the present invention to provide a method for the production of patterned ultra-thin films for the selective adhesion and outgrowth of cells.

It is another object of the present invention to provide novel cell culture apparatus which contains a patterned ultra-thin film for the selective adhesion and outgrowth of cells.

It is another object of the present invention to provide a method for culturing cells such that the cells adhere and grow on a surface in a pattern which substantially corresponds to a predetermined pattern on the surface.

It is another object to provide body implants which contain a patterned ultra-thin film for the selective adhesion and outgrowth of cells.

It is another object of the present invention to provide a cell-based microsensor which contains a patterned ultra-thin film for the selective adhesion and outgrowth of cells.

These and other objects, which will become apparent in the following detailed description have been achieved by the inventors' discovery that culturing cells on a surface, having a patterned ultra-thin film in which at least a portion has an exposed surface of at least one cell adhesion promoter and at least another portion of the film has an exposed surface of a cell adhesion inhibitor, results in a pattern of cell adhesion and outgrowth which substantially corresponds to the pattern of the cell adhesion promoter and inhibitor of the ultra-thin film.

The inventors have also discovered that such ultra-thin films are useful as surfaces for body implants, cell culture devices, and cell-based microsensors. In addition, the inventors have discovered that such patterned ultra-thin films may be produced by a process comprising:

(i) coating a substrate with a compound to obtain an ultra-thin film which is reactive to radiation and having an exposed surface of at least one cell adhesion promoter or inhibitor; and (ii) irradiating the ultra-thin film in a pattern to obtain an irradiated film with a surface region in which at least a fraction of said promoter or inhibitor has been removed.

In another embodiment, the process may further comprise treating the irradiated film with a second compound to bind to the surface region in which at least a fraction of the promoter or inhibitor has been removed.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 3c illustrates SK-N-SH cells which have adhered to EDA on an orthogonal EDA/13F UTF. The geometry of the EDA/13F pattern corresponds to a portion of the mask like that shown in FIG. 3a;

DETAILED DESCRIPTION OF THE PREFERRED EMBODIMENTS

Figure 1A:
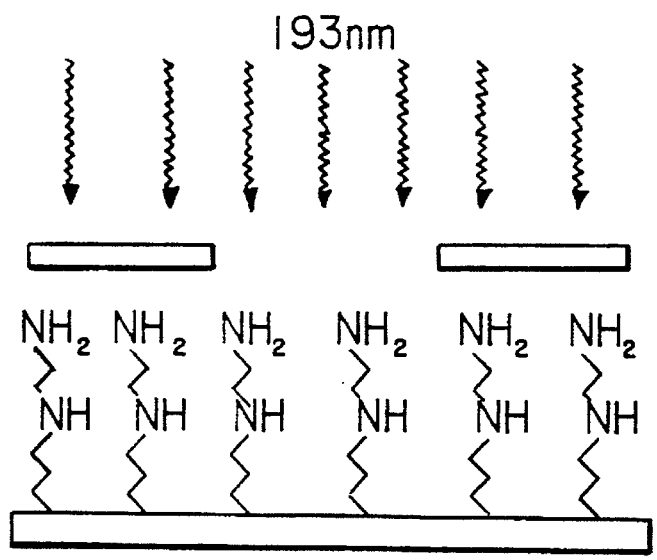
FIGS. 1a–c illustrate schematically the procedure for the preparation of a patterned EDA/13F surface: (a) The metallized surface of a fused silica photolithographic mask was tightly positioned against an EDA-coated glass microscope slide; (b) A 15 J/cm$^2$ DUV exposure resulted in photochemical modification of the EDA in the unshielded regions to produce a pattern of oxidized surface molecules, which are collectively represented as free hydroxyl groups on the glass surface; (c) Immediately following DUV exposure, the glass slide was immersed in a 1% mixture of 13F in toluene to selectively remodify the previously-exposed regions, producing orthogonal EDA/13F UTFs.

Several terms are used in this application which have meaning as described below. "Ultra thin film" refers to films or layers which are at least one molecule thick. Often, the films used are thinner than about one quarter of the wavelength of light used to expose the substrate, and may be as thin as a monomolecular layer.

"Radiation reactive material" as used herein is a material reactive to radiation that can absorb radiation used to expose it and which undergoes a modification as a result of absorption of the radiation. Preferably, the radiation reactive material will absorb light with a wavelength of less than 400 nanometers. Most preferably the radiation reactive material will have an absorption maximum at the wavelength used to expose the material. Radiation reactive materials include organic, inorganic and polymeric materials. Polymeric materials include polyethers, polyurethanes, polysulfones, polystyrene, polyamides, polymethacrylates, polybutadienes, polyethylene terephthalate, paraffin, polyisoprene and blends and copolymers of such materials. Other materials include chlorosilanes, methoxysilanes, ethoxysilanes, silazanes, titanates, zirconates, and the like.

"Irradiation" can be any electromagnetic wave which causes a change in the reactivity of the surface to be treated. In conventional photolithography with thick (ca. 1 micron) photoresists, the overall resolution of the process is directly proportional to the wavelength of light which causes the change in the reactivity of the layer or film. Therefore, it is preferred to use irradiation which would be shorter than 500 nm in order to achieve a theoretical resolution of less than 0.5 microns and even more preferred to use irradiation shorter than 250 nm in order to achieve a theoretical resolution of less than 0.25 microns in the claimed process. Because this process can also utilize ultra-thin films that are considerably thinner than the wavelength of the patterning radiation, it is possible to use near-field optics to achieve potential feature resolution on the order of tens of nanometers. A discussion of near-field optics can be found in the manuscript by U. Durig, et al., IBM J. Res. Develop., Vol. 30, pg. 478 (1926) entitled "Near-Field Optical Scanning Microscopy with Tunnel-Distance Regulation". Resolution refers to the space between deposited lines such as metal lines or line width deposited. Irradiation in patterns can be accomplished by any of the known conventional techniques such as direct write electron or laser beam, projection step and repeat, proximity printing, contact printing.

A "patterned ultra-thin film" is meant to refer to a structure built up on the surface of a substrate which conforms to a preselected pattern. The pattern is that pattern created by patterned irradiation. The molecular assembly can be a single layer of one material or multiple layers of the same or different materials. These materials include inorganic, organic materials, as for example semiconductive, metallic or combinations of these materials.

For example, irradiation reactive material such as a particular chlorosilane or methoxysilane can be exposed and then a second silane can be built up selectively in the most reactive areas. If the first reactive material is an amino silane and a silane with a fluorinated group is the second reactive material, in this case the silane with the fluorinated group will be bound to the exposed areas and therefore, the amino silane will be bound only in the unexposed areas. Assemblies can be built up further by introducing a second molecule which will bind to the most reactive of the spatially different areas of reactivity and a third layer may be built up in the same manner which can then have a fourth layer built onto it.

The present patterns contain spatially different areas of reactivity. "Spatially different areas of reactivity" are composed of high resolution patterns of different chemical moieties created when a radiation reactive material at its surface layer, is exposed in a pattern with the proper irradiation wavelength. The spatially different areas of reactivity can be side by side in a single plane or in three dimensions and organic, inorganic, polymeric, metallic or semiconductive materials can be involved which are at least one atom thick. The organic materials can include aliphatic unsaturated and aromatic hydrocarbons, methacrylates, amines, halocarbons, esters, ethers, polymers and others. The inorganic materials can include silicon oxides, titanium oxides, zirconium oxides, aluminum oxides, platinum oxide, copper oxide and the like as well as mixtures thereof.

For the purposes of the present invention, the terms "promoter" and "cell adhesion promoter" refer not only to the functional group which is exposed on the surface of the ultra-thin film and promotes the adhesion of cells, but also to the compound which is used to form the ultra-thin film having the exposed surface of a cell adhesion promoter. However, it is to be understood that when the term "promoter" is used in connection with removal by irradiation, at least the functional group which is exposed on the surface and promotes cell adhesion is being removed. The terms "inhibitor" and "cell adhesion inhibitor" are to be analogously interpreted.

Thus, in one embodiment, the present invention relates in general to the production of patterned films on solid substrates with use of one or more patterned irradiation steps. More particularly, in one embodiment, the invention pertains to UTFs that provide desired surface characteristics on substrates to which the films are strongly adherent. Yet even more particularly, the invention concerns procedures whereby areas of widely varying reactivity can be created with sub-micron lateral resolution on the substrate surface. The invention enables the selective deposition of biological cells and control of their outgrowth and development on semiconductor, dielectric, polymeric, or conductive surfaces as a direct consequence of differential adhesive properties.

According to the invention, the process of producing patterned molecular assemblies on a substrate is carried out by providing a substrate having at least one layer of radiation-reactive material having substantially equal reactivity over a surface. The surface of the radiation-reactive material is exposed to patterned radiation to create first and second areas of different reactivity. One additional layer of material may be built directly next to one of said first layer to create a patterned substrate with desired areas of different reactivity.

The invention can comprise a process for producing differential cell-adhesive UTFs on solids by causing a layer or film on the surface of the substrate to be altered in its adhesivity. Adherent cells grow and develop only in those regions having a sufficient adhesivity. Preferably, the substrate is of the kind having a polar functional group at its surface and the monomolecular films are self-assembling films which are deposited on the surface of the substrate and can be a monomer or polymer. Yet more preferably, the surface of the self-assembling films are of the type which either promote cell adhesion or inhibit cell adhesion and are capable of renewed reactivity upon exposure to deep ultra-violet light, so that a subsequent self-assembling film can be deposited selectively in the same or similar plane as the first self-assembled film, creating high-resolution patterns of cell adhesion promoters and cell adhesion inhibitors. It is a feature of this invention that high-resolution patterns of biological cells which can be spaced apart distances of 10 µm or less can be made on a variety of technologically relevant substrates including semiconductors, metals, biocompatible polymers, and ceramics.

In a preferable embodiment, cells from established lines or dissociated tissues are plated on patterned substrates in a suitable culture medium. Biological cells only adhere to and develop on those regions of the film that have sufficient adhesivity to bind the cells. After a period of time (20 minutes to 2 hours), non-adherent cells are rinsed from the substrate with culture media. When selectively adhered cells are cultured on said substrate in vitro, they develop only in defined substrate regions.

Preferably, the spatial dimensions of the defined substrate adhesivity are designed to effect the initial adhesion, outgrowth, and interaction of, for example, explanted mammalian neurons. In a very preferable embodiment, the substrate pattern is designed to position individual or groups of cells on or near transducer elements which selectively activate and/or measure physiological events within the cells in an addressable manner. This embodiment of the invention is particularly relevant to the selective adhesion of cells to microelectrodes, photodiode arrays, and fluorescence or chemiluminescence detectors. In this embodiment the present invention contributes to the fabrication of new classes of biosensors capable of detecting families of neurotoxins and neurotransmitters, or assessing the efficacy of experimental drugs.

In another very preferable embodiment, the substrate is a biomedically relevant material such as a metal or polymer which is suitable for use in implant devices. The substrate pattern is designed to allow certain cells to selectively adhere and develop on the device in order to influence the subsequent development of tissue on or inside of the device. The device may, for example, be an artificial tube which contains a microadhesive repair template for the outgrowth of damaged neurons, or which interfaces neurons to a prosthetic device interface. In another example, the device might be a surgical implant material used as an artificial ligament or bone material. The selective patterning of osteoblast cells on such materials may be used to improve biocompatibility and improve fixation of the material in native bone.

In a first embodiment, the present method for preparing the present ultra-thin films for the selective adhesion and outgrowth of cells involves coating a substrate to form an ultra-thin film with an exposed surface of a cell adhesion promoter, which on irradiation is converted to a region devoid of the promoter,, and then irradiating through a mask to form an area which does not promote cell adhesion, in a pattern corresponding to the transparent part of the mask. Thus, coating glass with a molecule, such as N-(2-aminoethyl-3-aminopropyl)trimethoxysilane (EDA), to form an ultra-thin film with an exposed surface of a cell adhesion promoter, such as —$NHCH_2CH_2NH_2$, and then irradiating with light of a suitable intensity and wavelength, through a mask, yields a surface with regions of cell adhesion promoter and regions devoid of promoter in a pattern, in which the pattern of the regions devoid of promoter corresponds to the transparent portion of the mask. Patterned surfaces produced by such a process are suitable for the selective adhesion and outgrowth of cells as shown by the results provided in Example 6 (vide infra).

Figure 1B:
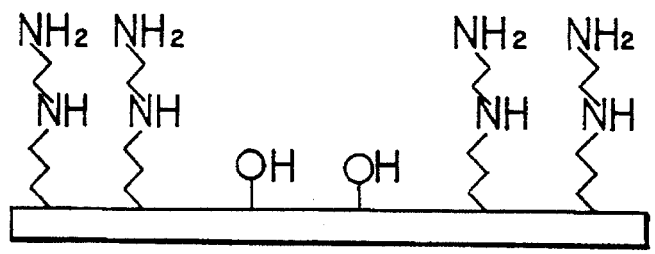
Figure 1C:
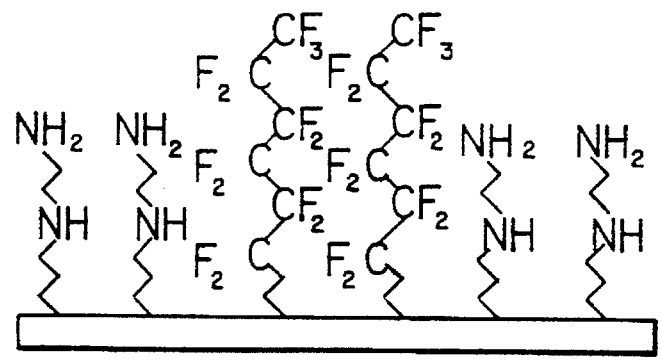

A preferred embodiment of the present process is shown in FIGS. 1a–c. FIG. 1a illustrates the irradiation through a mask of a substrate which has been coated with a cell adhesion promoter to form an ultra-thin film which has an exposed surface of —$NHCH_2CH_2NH_2$ groups. After irradiation, a region which is devoid of cell adhesion promoter is formed as shown in FIG. 1b. The process may then be continued by treating the surface of 1b with a reagent to bind to the exposed region with a cell adhesion inhibitor as shown in FIG. 1c. Of course, it is to be understood that the present process does not require that the cell adhesion promoter be coated first. Thus, the process depicted in FIGS. 1a–c may be varied to include a process in which the substrate is first coated with a radiation-reactive cell adhesion inhibitor, then the coated surface is irradiated to form a reactive region, and the surface is treated with a second compound to remodify the reactive region with a cell adhesion promoter.

Thus, by converting the exposed region to either a second cell adhesion promoter or inhibitor, it is possible to improve the selectivity of adhesion of the cells to the promoter region. For the purposes of the present application, the selectivity of cell adhesion for a particular pair of cell adhesion promoter and inhibitor is defined as the percentage of cells adhering to the promoter region out of the total number of cells plated on a surface containing equal areas of the promoter and inhibitor and on which the individual regions of promoter and inhibitor have areas larger than the diameter of the cells being plated.

A surface exhibits selective adhesion if the surface exhibits an adhesion selectivity of at least 75%, preferably at least 90%, more preferably at least 98%.

In another embodiment, either or both of the cell adhesion promoter or inhibitor surfaces may comprise two or more different cell adhesion promoters or inhibitors. Regions containing two or more cell adhesions promoters may be prepared by simply coating with a mixture of compounds containing cell adhesion promoter or inhibitor functional groups. However, because of the lack of stoichiometric control owing to different rates of reactivity, it is preferred that regions containing two or more promoters or inhibitors be prepared by a process in which the substrate is first coated with a first promoter and the surface is then, either with or without a mask, irradiated with light of suitable wavelength and sufficient intensity to only partially bring about the reaction of the exposed region. In this way, it is possible to remove only a portion of either the promoter or inhibitor as demonstrated in Example 1. After the irradiation step, the surface may be treated with another compound to convert the new reactive sites to a second promoter or inhibitor. Thus, by controlling the exposure of the surface to the irradiation, it is possible to remove the desired amount of the first promoter or inhibitor in the exposed region and thus precisely control the relative amounts of the first and second promoters or inhibitors in the exposed region. Of course, this procedure may be carried out iteratively to prepare regions which contain more than two different promoters or inhibitors.

Thus, it is possible to prepare patterned surfaces for the selective adhesion and outgrowth of cells of any desired pattern which is attainable by photolithography. It is to be understood that the present surfaces are not limited to those which contain regions of only one type of promoter and one type of inhibitor. Thus, the present surface may possess three or more different types of exposed surfaces. For example, it is possible to prepare a surface which contains a region A having an exposed surface of a first promoter, region B having an exposed surface of a second promoter, and region C having an exposed surface of a third promoter, etc.

The present invention also relates to cell culture apparatus which contain at least one patterned surface for the selective adhesion and outgrowth of cells. As mentioned above, biological cells normally develop randomly on the surface on which they are plated and the ability to construct precise two-dimensional arrangements of cells in vitro is desired. Thus, substrates having defined geometric patterns of adhesion may be used to predispose plated cells to develop into a desired structure or functional arrangement. Examples of such devices include petri dishes, and culture flasks. Further, such devices may be used, for example, to define the dimensions of capillary-like structures obtained by the culture of endothelia cells (Robinson et al, in vitro *Cell. Dev. Biol.*, vol. 26, p. 169 (1990)). In such a device, a surface would be coated with at least one region of cell adhesion promoter with a width which corresponds to the desired outer circumference of the microvessel. Alternatively, the present apparatus may be used to define the geometry and specificity of neuronal or neuromuscular synapse formation. For this purpose it may be desirable that the patterned surface contain a "T"-shaped region of the promoter such that the neuron may make a right-angle contact with the muscle cell. Selective adhesion of the muscle cell and neuron to the different areas of the promoter region may be accomplished by physical masking (with, e.g., a cover slip) of one region while plating with the first cell and then removing the mask while plating with the second type of cell.

The present apparatus may also be used to define the geometry of the formation of calcified tissue from patterns of precursor (stem or osteoblast) cells, the directional orientation of the cell body axis for controlled application of vectorial (electrical and magnetic) fields, and the influence of various types of cell adhesion promoter geometries on the morphological development of a single cell. In regard to the definition of the geometry of the formation of calcified tissue, it may be desirable to arrange the pattern of cell adhesion promoter regions such that the stem or osteoblast cells form a sheet rather than clumps. In regard to defining the influence of the geometry of the cell adhesion promoter on the morphological development of a cell, it may be desirable to arrange the cell adhesion promoter regions in the geometry of a diamond, a triangle, a circle, or a rectangle. Of course, the cell promoter regions may be arranged in geometries which represent combinations of one or more of the above-mentioned types and which may be connected by narrow regions of cell adhesion promoter. The present apparatus may be any of the following provided that at least one patterned surface according to the present invention is present: a microscope slide, a cover slip, an electron microscopy sample holder, a petri dish, a culture flask, or a culture tube.

In another embodiment, the present invention relates to cell-based biosensors. The ability to precisely position cells on a substrate may be used to permit the physical addressability of individual cells in a defined, two-dimensional architecture. It has been previously shown that the electrical activity of cultured cardiac (*Thomas et al, Exptl. Cell Res.*, vol. 74, pp. 61–66 (1974) and *Israel et al, Am. J. Physiol.*, vol. 247, pp. H669–H674 (1974)) and neural (*Pine, Jour. Neurosci. Meth.*, vol. 2, pp. 19–31 (1980) and *Gross et al, Jour. Neurosci. Meth.*, vol. 5, pp. 13–22 (1982)) cells may be stimulated and monitored using substrate-mounted microelectrodes. Stimulation of these cell types results in a transient depolarization of the resting membrane potential causing an ion flux which may be detected as a change in the local potential profile around the cells. However, in the above-described apparatus, cells are randomly plated onto microelectrode arrays. As a result, the signal obtained decreases as a function of distance from the microelectrode. Hence, low level responses, in neural cells (i.e., not resulting in action potentials), are not detected. Recently, a method for measuring the electrical responses (*Regehr et al, Jour. Neurosci. Meth.*, vol. 30, pp. 91106 (1989)) in which a relatively large (40–200 μm diameter soma) neuron is manually positioned over substrate-mounted microelectrodes has been reported. An adhesive substrate coating is used to promote a high impedance seal between the cell membrane and the electrode, thus forming a "loose patch". The value of the technique depends on the formation of the high impedance seal between the cell membrane and the measuring electrode (in the substrate) to prevent short circuiting to the reference electrode (in the medium), and to allow the capacitive charging of the membrane to be induced or accurately detected with the measuring electrode. However, as noted above, the microsensors of the prior art require that the neurons be manually positioned over the substrate-mounted microelectrodes.

In the microsensors of the present invention, the cells are positioned in the desired areas by coating the appropriate areas with a cell adhesion promoter. Thus, the present microsensors contain a substrate which is coated with at least one region of a cell adhesion promoter which is located sufficiently close to a physical transducer that the transducer may either receive signals from or stimulate the cell adhering to the promoter region. Examples of suitable transducers include but are not limited to microelectrodes, field effect transistors, photodiodes, piezoelectric materials, liquid crystals, conductive polymers, fiber optic devices, and spectroscopic apertures. As noted above, such transducers may be used to either stimulate or receive signals from the cell. In one embodiment, the present microsensors have at least one cell adhesion promoter region with a surface area which permits the adhesion of only a single cell and this region is located on or near the transducer. Preferably, the cell adhesion promoter region is directly attached to the transducer. Of course, the present microsensors may contain more than one transducer. In this case, it is preferred that each transducer be individually addressable.

In a second embodiment, the present microsensors contain a cell adhesion promoter having sufficient area and a distinct pattern to permit the adhesion of a plurality of cells in a defined architecture. In this embodiment, the adhered architecture of cells within the cell adhesion promoter region may be either stimulated or detected with one or more transducers. Of course, in such an embodiment, each transducer may independently of the others act as either a stimulator or a detector. In this manner, for example, it is possible to construct a device in which a network of neurons may be stimulated at one end by a transducer while a second transducer is used to detect the resulting signal, if any, at a second end. Thus, the present microsensors may be used to assay the effect of stimuli drugs and insults on intercellular communication (in this case synaptic communication) may be determined.

It is to be understood that the present microsensors may also be used in conjunction with fluorescent or chemiluminescent probes and assays. In this case, it is preferred that at least one of the transducers be suitable for detecting such luminescence.

The present microsensors thus permit the pharmacological screening of a large number of cells without the difficulties encountered with the conventional techniques, such as the use of a patch clamp.

In another embodiment, the present microsensors may be used to detect levels of bioactive materials in a sample or environment. Although the present microsensors may be used in conjunction with any suitable cells, when the microsensor takes the form of a neurotoxin biosensor, it is preferred that the biosensor be used in conjunction with an easily cultured neuronal cell line such as that described in Ronnett et al, Science, vol. 248, p. 603 (1990).

In another embodiment, the present invention relates to prosthetic implants which contain at least one patterned surface for the selective adhesion and outgrowth of cells. As demonstrated in the examples, the directional outgrowth of human neuroblastoma cells may be directed by the use of high resolution adhesive patterns. Thus, the present implants may take the form of a device for the directed growth of neurons. In one embodiment, such a device may take the form of a tubular implant for axon regeneration in severed nerves. Conventional tubular implants are hollow tubes which may optionally be filled with a matrix but do not possess a patterned surface for the selective adhesion of cells (Fields et al, Progress in Neurobiology, vol. 33, pp. 87–134 (1989). In such devices, the process of axon regeneration proceeds via a multi-step process which first involves the bridging of the gap between the proximal (relative to the spinal cord) and the distal ends of the severed nerve by a narrow fibrin-rich matrix. Eventually, fibroblasts and Schwann cells envelope the matrix strand. The latter of the cell types is essential for the adhesion and extension of the regenerating axons from the proximal to the distal end of the tube. Many axon tips eventually transverse the tube and reinnervate target muscles via the remaining Schwann cell network in the distal end of the nerve. However, much of the effectiveness and specificity of innervation is lost, due to the amount of time required for the reappearance of Schwann cell pads in the tubes (ca. 10 days) and crossover of axon tips from one cross-sectional region of the proximal stump to non-corresponding Schwann cell pathways which remain in the distal stump.

In the present tubular implants for axon regeneration, the cross-sectional correspondence is improved by providing a pattern on at least one surface of the tubular implant for the selective adhesion and growth of Schwann cells. In this embodiment, the Schwann cells may be pre-adhered to linear cell adhesion promoter regions from the proximal to distal end and thus provide a pathway for the regeneration of the neurons. In a preferred embodiment, the present tubular implant takes the form of a cigar-like object in which a sheet of a material on which spacers of a specified height and placed at a specified distance and running the length of the sheet is rolled in a width-wise direction to form a cylinder which when viewed from one of the ends reveals a spiral. In this embodiment, a strip of cell adhesion promoter is formed between each spacer and runs parallel to the spacers.

Figure 5A:
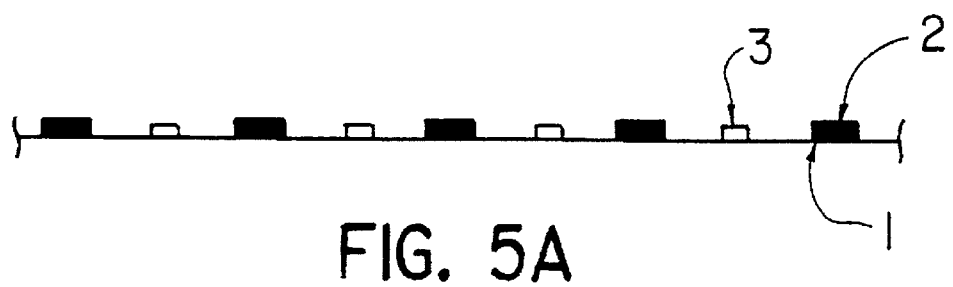
FIG. 5 illustrates a tubular implant for the regeneration of neurons according to the present invention.
Figure 5B:

A process for producing such a cigar-like tubular implant is shown in FIGS. 5a and b. Thus, by rolling a sheet of a biocompatible material 1 in which parallel and alternating spacers 2 and patterned strips of cell adhesion promoters and, optionally, adhesion inhibitor regions 3 are previously formed into a cigar-like tube, results in a device in which there are numerous well defined channels for the adhesion of the Schwann cells and the subsequent regeneration of the neurons.

Transducers, such as silicon chips with vias, have also been utilized to facilitate the regeneration of severed nerves and the connection of nerves with external stimulating and detecting devices. Thus, the present implant may also take the form of a silicon chip with a via or transducer interface which contains an exposed surface of cell adhesion promoter in the via or in the area leading to the via or transducer.

In addition, the present invention relates to templates for the directed growth of a new organ, called an organoid or a neo-organ. Conventionally such templates are prepared by coating a biocompatible material, e.g., teflon which is in a suitable form such as a tube. Currently the growth of cells on the template is stimulated by coating the tube with a material such as gelatin which is then matted into a sponge-like shape and then coating with various growth factors. In the present templates, the need to coat the template with growth factors is obviated by the use of cell adhesion promoters rather than growth factors. In addition, the present invention permits the template to be coated with a desired pattern of cell adhesion promoters so that the pattern-wise growth of cells in the neo-organ may be achieved. Thus, the present templates may be coated with a pattern of cell adhesion promoters to promote the adhesion of a particular pattern of, e.g., epithelial or endothelial cells.

The present invention permits, in a very simple manner, the patterning of UTFs in combination with DUV exposure to define the two dimensional cell-adhesivity of a solid substrate through direct patterning of a layer of oriented surface molecules. Because of the simplicity and generality of the process, and the controlled spatial resolution of cell adhesivity available, this fabrication method is of potential use in any application where the non-random positioning of cell populations is necessary or desired. The disclosed process is significantly simpler to perform than other existing techniques, due to a reduction in the number of processing steps required to fabricate a substrate with high resolution patterns of selective cell adhesivity. Only 8 processing steps are required, compared to 18 or more if conventional lithographic methods are used.

The generality of this process toward the type of substrates that either intrinsically possess, or are treated to have, polar functional groups at the surface has been demonstrated in U.S. patent application Ser. No. 07/182,123, filed Apr. 14, 1988 and U.S. patent application Ser. No. 07/022,439, filed Mar. 6, 1987, which are incorporated herein by reference. The substrate types include, but are not limited to: silica (quartz and glass), silicon (doped and undoped), other semiconductors (e.g., germanium, gallium arsenide), organic polymers such as epoxy resins, polystyrenes or polysulfones, metals such as aluminum and platinum, and metal oxides such as alumina, and native or modified biomedically-relevant polymers such as silicones, rubber, fluoropolymers, polyesters, acrylic copolymers, polyglactin and polyacetates.

Limitations to resolution in conventional optical lithography arise from the use of relatively thick films (1.0–1.5 μm thick) which suffer from defocussing of the image in the film, the occurrence of standing waves in the film, Rayleigh scattering from film inhomogeneities, and a reduced control of the spatial extent of photoreactions. The present process minimizes these problems through the use of ultra-thin films, which are significantly thinner than a quarter of the wavelength (less than 50 nm) of the light used to expose them. The above mentioned problems are also minimized by using radiation of the shortest possible wavelength to which the resist is sensitive. Most of the currently used high resolution photosensitive materials absorb near UV (i.e., 320 to 400 nm) light. Few known photoresists are useful in the DUV (200 to 320 nm) or the vacuum-UV (below 200 nm) regions. The process disclosed here uses, but is not limited to 193 nm light, and is therefore capable of higher resolution than conventional photoresists. Many light sources for UV irradiation are available, including mercury lamps, xenon lamps, deuterium lamps, surface plasma discharge sources, Nd-YAG lasers, excimer lasers, and optical harmonics generated from the sources.

There are numerous classes of substances whose molecules, under appropriate conditions, self-assemble to form thin films. In general, those self-assembling molecules characteristically include a polar end, a non-polar opposite end with a reactive moiety at or near the terminus, and an intermediate region typically composed of saturated or unsaturated hydrocarbon chain or may not have an intermediate region. The spacer can be monomeric or polymeric.

The class of polar end groups (which interact with the polar surface of the substrate) include silanes of the $R_nSiX_m$ type where R is an organic functional group;

n is a number between 1, 2 or 3;

m= 4–n; and

X is a halogen, alkoxy or amino group.

The class of polar end groups further includes carboxylic acids, acid chlorides, anhydrides, sulfonyl groups, phosphoryl groups hydroxyl and amino acid groups.

The class of non-polar end groups include olefins, acetylenes, diacetylenes, acrylates, aromatic hydrocarbons, methacrylates, methyl, perfluorinated hydrocarbons, primary amines, long chain hydrocarbons and esters.

While specific films have been exemplified using specific silanes that either promote or inhibit cell adhesion, many other types of films can be applied to surfaces to control their cell adhesivity. Alternative examples of commercially available aminosilanes that may be used to promote cell adhesion are: trimethoxysilane N-(2-aminoethyl-3-aminopropyl)trimethoxysilane (EDA), 11-aminoundecyltrimethoxysilane, 3-aminopropyltrimethoxysilane, 3-aminopropyltriethoxysilane, 3-aminopropylmethyldiethoxysilane, 3-aminopropyldimethylethoxysilane, 3-(1-aminopropoxy)-3,3-dimethyl-1-propenyltrimethoxysilane, 6-(aminohexylaminopropyl)trimethoxysilane, N-(2-aminoethyl)- 3-aminopropylmethyldimethoxysilane, bis[3-(trimethoxysilyl)propyl] ethylenediamine, trimethoxysilylpropyldiethylenetriamine, and (aminoethylaminomethyl)phenethyltrimethoxysilane (DAP).

Alternative examples of commercially available fluorosilanes that might be used to inhibit cell adhesion are: tridecafluoro-1,1,2,2-tetrahydrooctyl)-1-dimethylchlorosilane (UTF-13F), tridecafluoro-1,1,2,2-tetrahydrooctyl)-1-trichlorosilane, tridecafluoro-1,1,2,2-tetrahydrooctyl)-1-methyldichlorosilane, tridecafluoro-1,1,2,2-tetrahydrooctyl)-1-triethoxysilane, (3,3,3-trifluoropropyl)-trichlorosilane, (3,3,3-trifluoropropyl)methyldichlorosilane, (3,3,3-trifluoropropyl)-dimethylchlorosilane, (3,3,3-trifluoropropyl)methyldimethoxysilane, (3,3,3-trifluoropropyl)-trimethoxysilane, (heptafluoroisopropoxy)propylmethyldichlorosilane, and (3-pentafluorophenylpropyl)dimethylchlorosilane (PFP). Other silanes that have been shown to inhibit cell adhesion (Klienfeld et al, *Jour. Neurosci.*, Vol. 8., p. 4098 (1988)) such as n-tetradecanetrichlorosilane, and n-[(3-trimethoxysilyl)propylethylenediaminetriacetic acid trisodium, along with other long acyl chain chloro-, methoxy-, and ethoxy-silanes, may also be used in the same manner as 13F.

In addition, epoxy silanes such as 3-glycidoxypropyltrimethoxysilane may be coated on the surface. Hydrolysis of the epoxide functionality results in the formation of a diol which inhibits cell adhesion as discussed in Massia et al., *Anal. Biochem.*, vol. 187, p. 292–301 (1990) and U.S. Pat. No. 4,562,157, which is incorporated herein by reference. Furthermore, the substrate may be coated with a silane containing a terminal olefin, which may then be converted to either an alcohol by hydroboration or a diol by either $KMnO_4$ or $OsO_4$ as described in U.S. Pat. No. 4,539,061, which is incorporated herein by reference.

Other classes of materials which may act as cell adhesion promoters or inhibitors include titanates. Titanates have the general formula $Ti(OR)_4$, where all four of the OR organic groups may be the same or different. These materials, and the related zirconate and aluminate classes of molecules, are recognized to be similar to silanes in that they spontaneously react with surface hydroxyl groups to give an organic monolayer which is covalently linked to the substrate with the evolution of an alcohol. An O-Ti bond is formed between the surface hydroxyls and the titanates. Titanates and zirconates with amino functionalities such as isopropyltri(n-ethylenediamino)ethyltitanate, neopentyl(dialiyl)oxytri(n-ethylenediamino) ethyltitanate, neopentyl(diallyl)oxytri(mamino)phenyltitanate, neopentyl-(diallyl)oxytri(n-ethylenediamino) ethylzirconate, and neopentyl(diallyl)oxytri(m-amino)phenylzirconate may be used to promote cell adhesion. Potential adhesion inhibitors for cells include titanates and zirconates where long fluorinated or unfluorinated alkylchains are present in the molecule. Other film forming materials that may be used to control cell adhesion include thiol or disulfide films that assemble on gold surfaces and carboxylic acids or acid chlorides that assemble on surfaces such as alumina and other metal oxides.

A preferred cell adhesion inhibitor is one which contains one or more fluorinated alkyl groups.

Alternative strategies for creating differential cell adhesive patterns may also involve the covalent attachment of cell adherent biological moieties to preformed UTF patterns. For example, covalently binding cell adhesive peptides such as Gly-Arg-Gly-Asp-Tyr and Gly-Try-Ile-Gly-Ser-Arg-Tyr to glass surfaces (Massia et al, *Anal. Biochem.*, Vol. 187, p. 292 (1990)) may be used in conjunction with a modification of the disclosed process described here. This modification involves the treatment of a surface with an adhesion inhibitor such as 13F, irradiation to form a pattern of regions devoid of the inhibitor, and treating the surface with a glycerolpropylsilane, such as 3-glycidoxypropyltrimethoxysilane, to bind to the region devoid of inhibitor. The attached glycerolpropylsilane may then be modified as described in Massia et al, *Anal. Biochem.*, Vol. 187, p. 292 (1990), incorporated herein by reference, creating a surface that will selectively adhere various cell types. The patterning technique allows sequential modification with more than two chemical functionalities. Thus, cell-specific adhesive patterns might be designed.

Although it is not possible to pattern many of the cell adhesion inhibitors mentioned above with 193 nm or longer wavelength light., it has been demonstrated in U.S. patent application Ser. No. 07/182,123, that these films can be patterned with shorter wavelength light, such as the 185 nm line from a low pressure mercury argon pen lamp, or with even shorter wavelengths. It should be noted that several of the above mentioned molecular species, such as DAP and PFP, are phenyl derivatives which will absorb at wavelengths longer than 193 nm and may be patterned at longer wavelengths, as described in U.S. patent application No. 07/182,123.

Suitable substrates include those which intrinsically possess or have been treated to possess polar functional groups. Examples of substrates which intrinsically possess polar functional groups include silica (quartz and glass), silicon (doped and undoped), other semiconductors (e.g., germanium, gallium arsenide) or organic polymers such as polyvinyl alcohol, and polyvinylphenol, or metals that intrinsically posses metal oxides such as platinum, aluminum, and titanium.

Examples of substrates which do not possess polar functional groups but which may be treated to form polar functional groups include poly(tetrafluoroethylene) (PTFE), polyethylene, polypropylene, and polystyrene. These polymers can have their surfaces modified by wet chemistry or radio frequency glow discharge plasma gas/liquid mixtures (RFGD) Vargo et al, *J. Polym. Sci. Poly. Chem. Ed.*, Submitted for publication (Dec. 1989)). An example is the modification of a normally chemically inert polymer poly(tetrafluoroethylene). PTFE has been modified by exposure to $Me_2SO$ solutions of the potassium salt of benzoin doanion with subsequent reactions to create surfaces containing covalently attached chlorine, bromine, hydroxyl, amino, and carboxylic acid functionalities (Costello et al, *Macromolecules*, Vol. 20, p. 2819 (1987)). Coupling silanes to these modified polymers may be achieved by the identical procedures used to couple silanes to inorganic substrates. Another process for modifying the surface of PTFE has been developed by Vargo et al. at the University of Buffalo (Vargo et al, *J. Polym. Sci. Poly. Chem. Ed.*, Submitted for publication (Dec. 1989). This process uses RFGD to modify the polymer. Recent work at the University of Buffalo has demonstrated that PTFE films modified by RFGD can be silanized with an 3-aminopropyltriethoxysilane (Hook et al, *Langmuir*, submitted for publication (May, 1990).

The ability to fabricate high resolution patterns of aminosilanes on defined, three-dimensional topographies and on platinum substrates was demonstrated in patent application 07/182,123. This, combined with the ability to control the selective adhesion of cells, allows the placement of cells within lithographically defined physical barriers such as microtrenches or wells, and onto substrate-embedded microelectrodes or photodiodes. For example, the bottom of the microtrenches and metal microelectrodes may be coated with a cell adhesion promoter while the sides and steps are coated with an adhesion inhibitor. This permits the precise positioning and controlled growth of cells on solid state microcircuitry.

Thus as described above, the outer layer of the substrate which forms the UTF which can be identical and integral with the body of the substrate or a separately applied film of a different material, can be polar or non-polar depending on the particular application.

The self-assembling thin film procedure utilized in the invention produces a uniform ultra-thin (less than about 200 nm) film having externally accessible reactive groups. Various methods can be employed to alter the reactivity of those groups. The choice of method may be determined in part or in whole by the desired resolution of the pattern to be produced in the film. Among the various methods is one of making the substrate unreactive or less reactive by photolytic cleavage at the molecular structure. As a corollary, olefins could be made more reactive to certain coupling agents (such as appropriately modified biomolecules, catalysts, and spectroscopic probes) by oxidation to produce hydroxyl groups. Alteration of reactivity in predetermined regions of the thin film allows chemical reactions to occur either (1) only in those regions whose reactivity has been altered, or (2) everywhere except the altered regions. Consequently, an important attribute of the invention is the ability to produce, with high resolution, sites in the film of different chemical reactivity such that only the reactive moieties are receptive to adhesion by another chemical moiety.

Other features of the invention will become apparent in the course of the following descriptions of exemplary embodiments which are given for illustration of the invention and are not intended to be limiting thereof.

EXAMPLES

EXAMPLE 1: EDA and 13F UTFs plated with Neuro-2A mouse neuroblastoma cells.

Glass microscope slides were cleaned just prior to the first film formation by immersion in 50:50 (vol:vol) HCl:methanol at room temperature for 30 minutes and rinsed three times with 18 MΩ water from a Barnstead NANOpure™ II deionization system with 0.22 µm filter. The substrates were then immersed into concentrated $H_2SO_4$ at room temperature for 30 minutes, then rinsed with 18 MΩ water five times. The last rinse was heated to boiling on a hot plate in a class 100 clean room.

The trimethoxysilane N-(2-aminoetbyl-3-aminopropyl)trimethoxysilane (EDA) was used as received from Huls of America, Petrarch Systems Silanes & Silicones. The glass slides were taken directly from boiling water and immersed in a fresh mixture of 1% (v:v) EDA/94% ($1 \times 10^{-3}$M acetic acid/anhydrous methanol)/5% 18 MΩ water for 15 minutes at room temperature. The substrates were then rinsed in anhydrous methanol and the residual solvent was removed from the film by baking the slides on a hot plate for 5 minutes in a class 100 clean room at a temperature of 120° C. The water contact angle of the film, as measured using the sessile drop method with 18 MΩ water, was found to be 17°–21° for all substrates treated with EDA but increased to an equilibrium value of 28°–32° within 3 hours.

The monochlorosilane, tridecafluoro-1,1,2,2-tetrahydrooctyl)- 1-dimethylchlorosilane (UTF-13F), was used as received from Huls of America Petrarch Systems Silanes & Silicones. 1% (v/v) stock solutions of the monochlorosilanes in SureSeal TM anhydrous toluene bottles (Aldrich) were mixed and stored in a Vacuum Atmospheres dry box under helium at room temperature. Glass microscope slides were cleaned as above, removed from boiling water in a class 100 clean room and immersed in A.C.S. certified anhydrous acetone (Fisher Chemical) twice and then immersed into anhydrous toluene. The substrates were immersed in an aliquot of the 1% UTF-13F stock solution for 30 minutes. The substrates were then rinsed in anhydrous toluene and the residual solvent was removed from the films by baking the substrates on a hot plate for 5 minutes in a class 100 clean room at a temperature of 120° C. The contact angle of these films was measured with 18 MΩ water and was found to be 92°–94° for all substrates treated UTF-13F.

Initial cell adhesion experiments were performed using glass microscope slides coated with a single molecular species. Mouse Neuro-2A neuroblastoma cells were incubated in minimal essential medium (MEM) with 10% fetal calf serum (FCS) at 37° C., in 5% $CO_2$. Prior to plating, cells were treated for 10 minutes with 0.1% trypsin and resuspended in either MEM alone or MEM with 10% FCS. Prior to cell plating, the UTF-coated slides were sterilized in 70% ethanol for 30 minutes. Cells were plated at a density of $8 \times 10^4$ cells/$cm^2$ and incubated for 20 minutes. Substrate surfaces were cleared of non-adhered cells by gentle rinsing with media from a pipet. Before and after rinsing the plated substrates, the slides were inspected using an inverted phase contrast microscope. In the presence of 10% FCS, greater than 98% of SK-N-SH neuroblastoma cells adhered when plated on EDA while less than 2% adhered to 13F. Adhesion to the EDA was unaffected by FCS but about 10–15% of the cells adhered as loosely bound clumps to 13F-treated slides in 10% FCS.

EXAMPLE 2: Exposure of EDA films to DUV and remodification with 13F.

Figure 2:
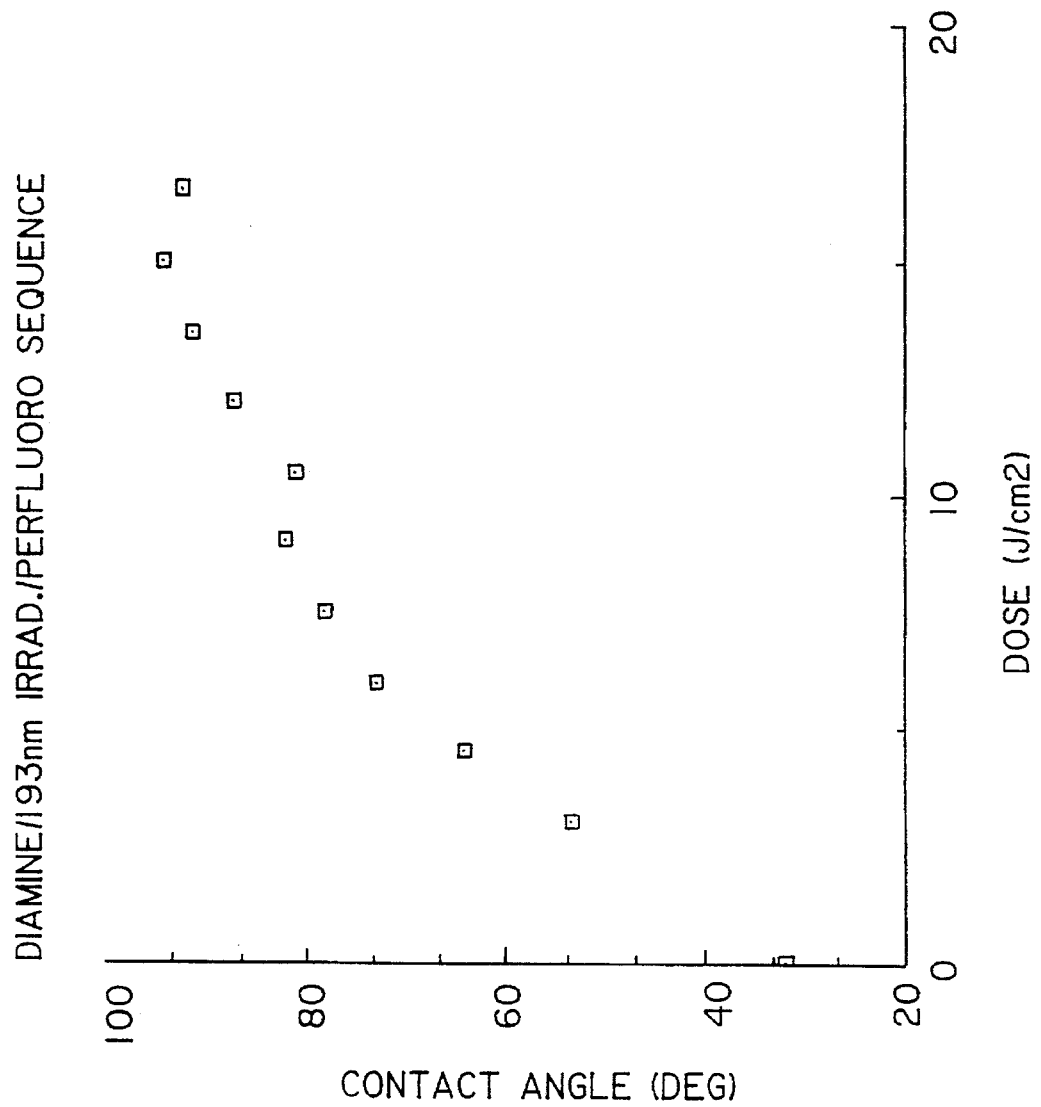
FIG. 2 illustrates the change in the contact angle of EDA-coated glass following exposure to increased amounts of DUV energy and subsequent remodification with 13F. Individual 1 cm$^2$ areas of EDA UTFs on glass microscope slides were exposed to 193 nm DUV from a pulsed argon fluoride excimer laser (10 Hz at 10–20 mJ/cm$^2$ per pulse), then exposed to a 1% solution of 13F in toluene. The water contact angle (as measured using the sessile drop method) of the remodified areas increased continuously from that corresponding to a pure EDA UTF (28°–32°) to that of pure 13F UTF (92°–94°) as the exposure was increased from 0 to 15 J/cm$^2$.

To determine if a protocol could be established for preparing patterned surfaces of EDA and 13F, pure UTFs of EDA were fabricated (as in example 1) and exposed to increasing dosages of 193 nm light from a pulsed (10 Hz at 15–20 mJ/$cm^2$ per pulse) ArF excimer laser (Cymer XL-2). The exposed substrates were then immersed in a 1% 13F treatment solution as described in Example 1. The water contact angle of the exposed and sequentially remodified areas and unexposed areas were measured and the results are illustrated in FIG. 2. The contact angle increased steadily from that corresponding to a pure unexposed EDA surface (28°–32°) to that of pure 13F (92°–94°) after an exposure of greater than 13 J/$cm^2$, indicating that the EDA had been completely replaced by 13F. However, 13F films did not undergo sufficient photochemical cleavage to yield a surface reactive to EDA. This was evidenced by only a slight change (86°–88°) in the contact angle, even when the film was exposed to dosages of about 20 J/$cm^2$. It should be noted here that, if it is desirable to have mixed films of EDA and 13F, they could be prepared at known surface concentrations following exposure to intermediate dosages of DUV radiation.

EXAMPLE 3: Low resolution EDA/13F patterns plated with mouse Neuro-2A and human SK-N-SH neuroblastoma cells.

Low resolution EDA/13F patterns were formed using the same procedure described in Example 2, except that a mask was positioned against the film. The mask allowed only a 15.9 $mm^2$ circular area to be exposed to a DUV dosage of 15 J/$cm^2$. The patterned EDA/13F substrates (see FIG. 2) were then plated with mouse Neuro-2A and human SK-N-SH neuroblastoma cells (J. L. (Biedler et al, *Cancer Res.*, Vol. 33, p. 2643 (1973) in MEM with 10% FCS as described in Example 1. After rinsing, greater than 98% of the Neuro-2A and SK-N-SH cells adhered selectively to the unexposed EDA treated areas. Less than 2% of either cell type adhered to the DUV-exposed film regions which remodified with 13F.

EXAMPLE 4: High resolution EDA/13F patterns plated with human SK-N-SH neuroblastoma cells.

Figure 3A:
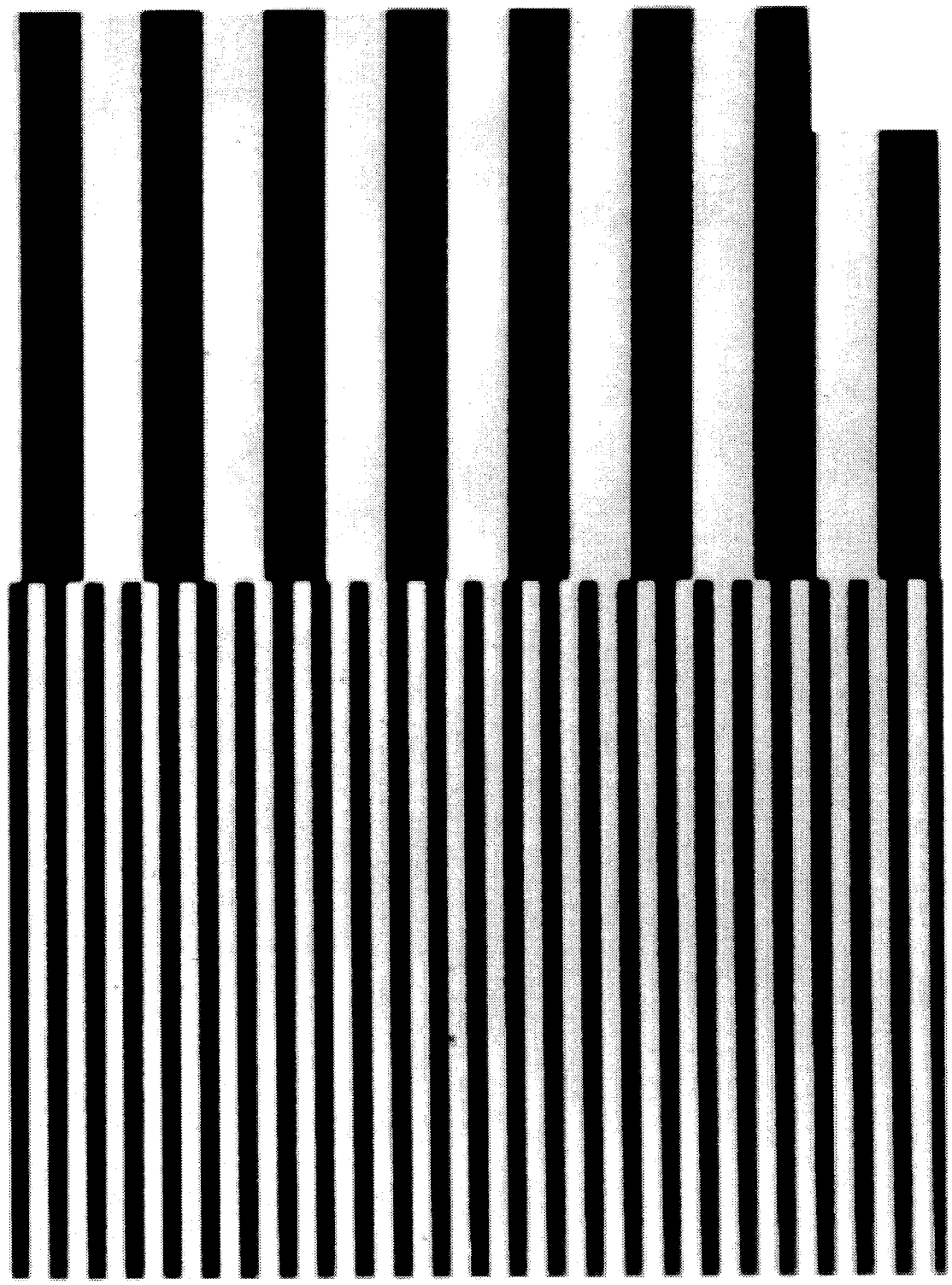
FIG. 3a illustrates a bright field micrograph of the metallized mask used to create the alternating EDA and 13F patterns. Dark regions correspond to the metal used to protect the underlying SAF-coated glass substrate. Light areas represent the DUV-transparent fused silica substrate of the mask and correspond to regions which are exposed and subsequently remodified with 13F. The interface between two line width/line spacing regions is shown. Larger dark lines are 40 μm wide, spaced at 40 μm. Smaller dark lines are 12 μm, spaced at 12 μm.

To create high resolution, alternating patterns of EDA and 13F, the metallized surface of a fused silica mask was tightly positioned against a glass slide coated with EDA. The mask, which had chromium line space pairings ranging from 10 to 100 μm, provided selective shielding of the film against a 15 J/$cm^2$ exposure (FIG. 3a). Following exposure, the slide was immediately immersed into a 1% 13F treatment solution, rinsed, and then baked as described in Example 1. Human SK-N-SH cells were plated, rinsed, and cultured in MEM with 10% FCS and 1.5 μM retinoic acid.

Figure 3B:
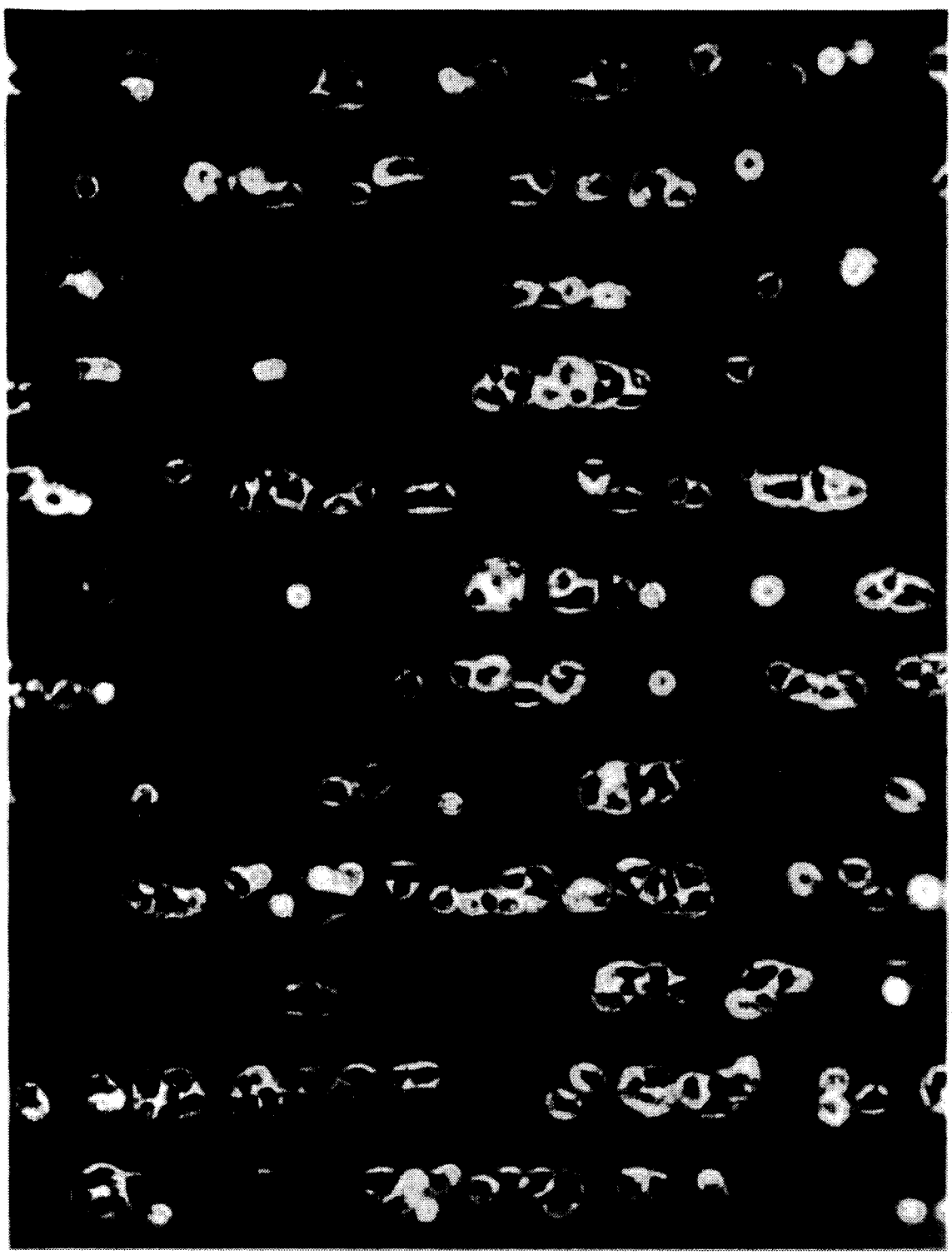
FIG. 3b shows SK-N-SH cells which have been selectively absorbed onto 40 μm wide lines of EDA. EDA-coated regions appeared lighter in phase contrast micrographs due to the absence of defect centers which were formed in the surrounding DUV-exposed glass substrate. Nearly 100% of the plated cells have selectively adsorbed to the EDA lines.
Figure 3C:
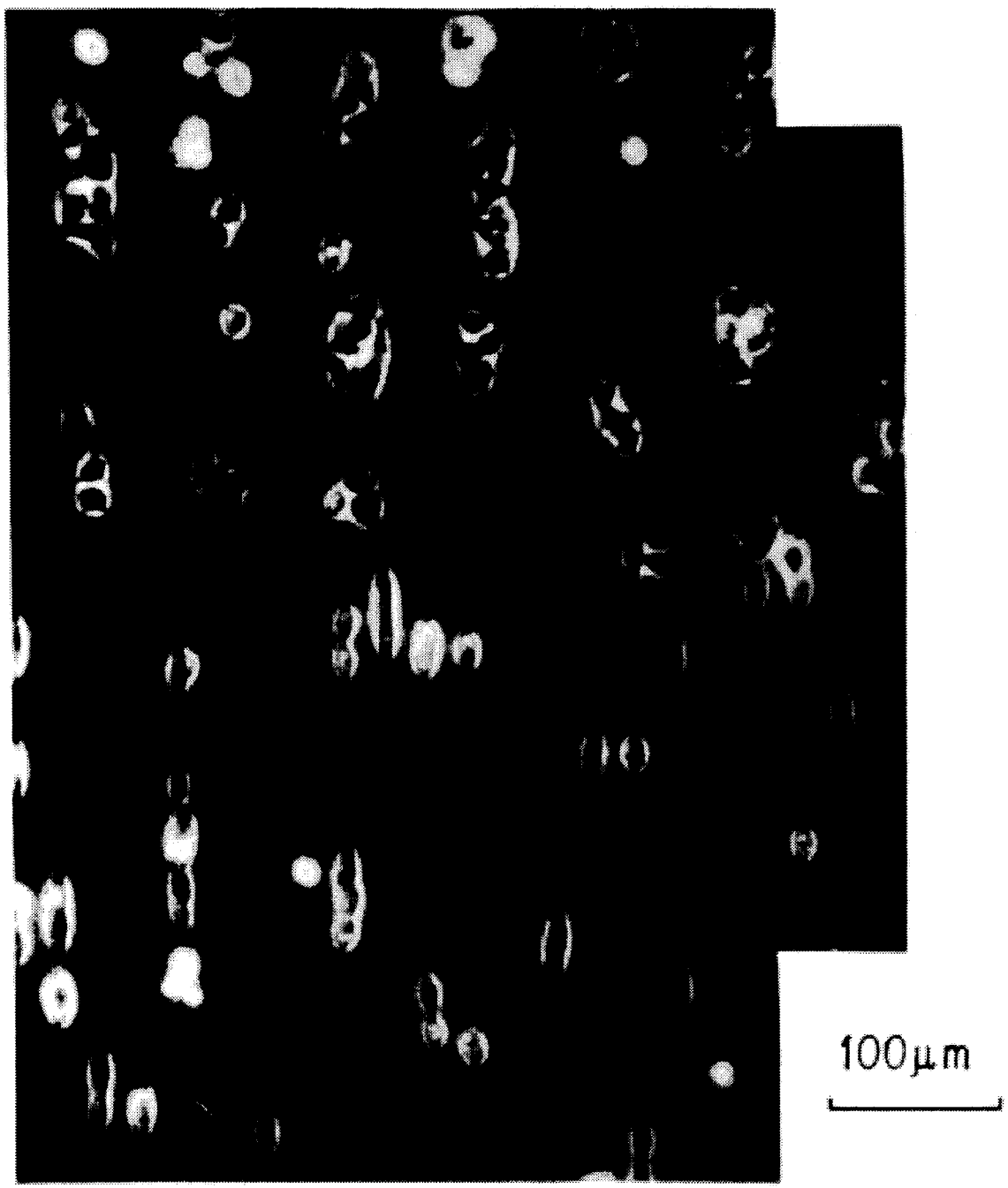

The effect of the substrate pattern on the morphology of SK-N-SH cells was clearly evident immediately after the slides were rinsed. Cells showed a nearly complete preferential adhesion to the patterned EDA regions, which appeared lighter due to the absence of color center defects which were formed in the neighboring areas of UV-exposed glass slides. On the 40 μm or greater wide lines of EDA (FIG. 3b), the cells maintained the same flattened spherical shapes which were normally observed on pure EDA substrates. However, in the 12 μm-wide EDA lines (FIG. 3c), the spatial resolution of the alternating EDA/13F patterns was finer than the spheroid cell diameters. This caused the cells to immediately elongate and adopt a morphology corresponding to the shape of the patterned EDA while minimizing interaction with the surrounding 13F surfaces.

Figure 4:
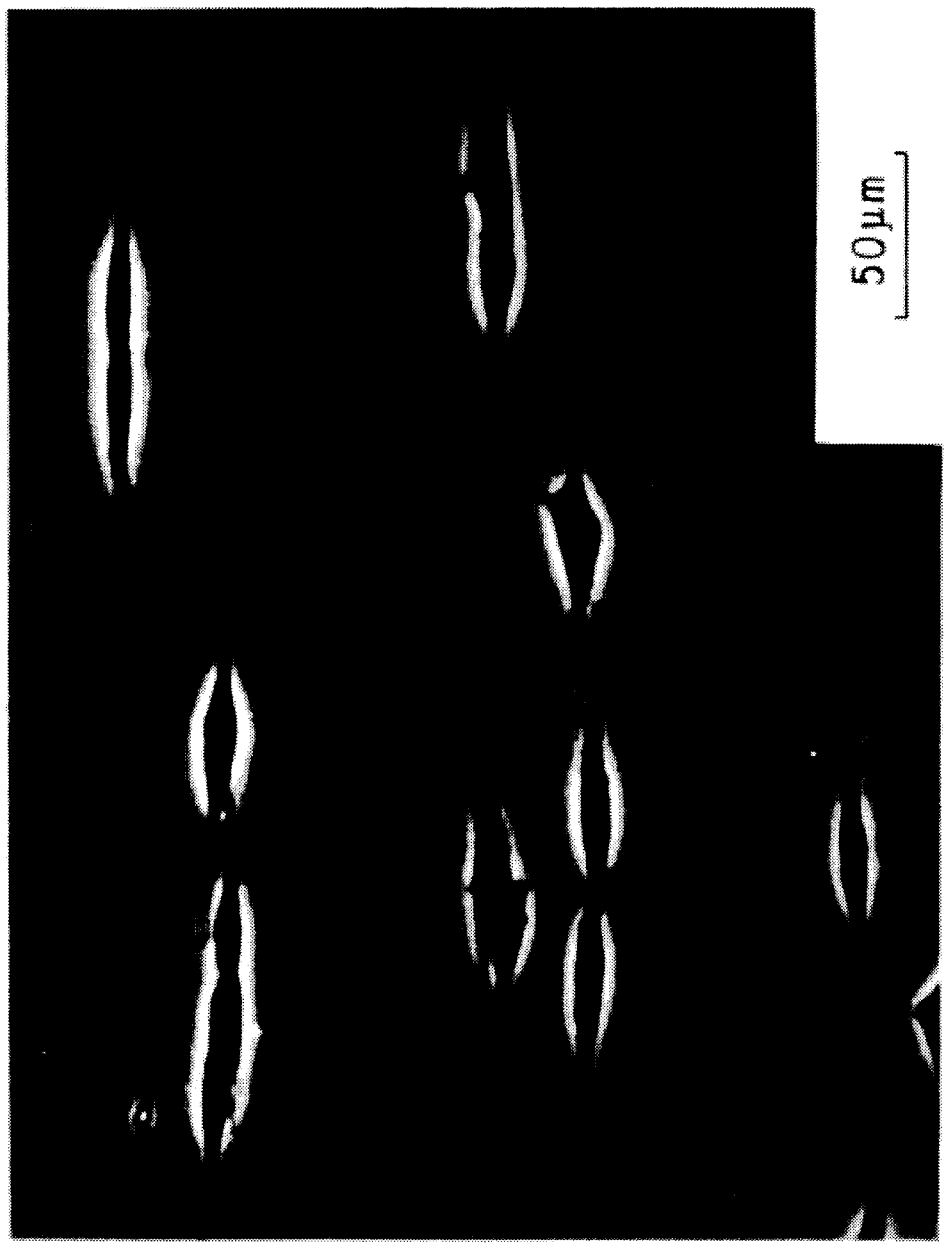
FIG. 4 illustrates SK-N-SH morphological development on 12 μm-wide EDA lines at 24 hours after plating. The direction of neurite outgrowth was determined by the geometry of the EDA component of the pattern.

After the patterned neuroblastoma cells had been incubated for 24 hours, neurite outgrowth was observed which was predominantly restricted to the EDA channels (FIG. 4). Clearly distinguishable growth cones were observed, indicating the suitability of the EDA substrates for cell growth. However, after 36 hours, an increasing number of neurites were observed to cross the 13F lines, as expected, due to the ability of fine filipodial processes at neurite tips to bridge narrow regions (less than 50 μm) of low-adhesivity substrata (Hammarback et al, *Dev. Biol.*, Vol. 117, p. 655 (1986) and Kleinfeld, *Jour. Neurosci.*, vol. 8, p. 4098 (1988)).

EXAMPLE 5: High resolution plating of dissociated mouse dorsal root ganglia (DRG) cells.

High resolution patterns of EDA/13F were fabricated as described in Example 4. DRG were isolated from fetal mice, dissociated, and plated onto high resolution EDA/13F patterns. Both neurons and glia from the heterogeneous cell mixture selectively adhered to 40 μm wide lines of EDA. After several days in culture, glial cell division and neuronal process outgrowth were predominantly restricted to the 40 μm wide EDA lines.

EXAMPLE 6: High resolution patterning of EDA treated glass substrate and plating of SK-N-SH neuroblastoma cells without backfilling of DUV-exposed regions with 13F.

Glass slides were cleaned, treated with EDA, and exposed to patterned irradiation as in Example 4, or cleaned and exposed to patterned irradiation without treatment of EDA. Both sets of slides in these experiments were not treated with 13F. These slides, as well as clean, unexposed slides, were plated with SK-N-SH neuroblastoma cells as described in Example 1. Before and after rinsing, the substrates were inspected using an inverted phase contrast microscope. Approximately 10% of the plated cells adhered to clean glass after rinsing whether or not the slides were exposed to DUV. The cell adhesion on glass which was exposed was independent of the irradiation pattern. Thus, there was no preferential adhesion to DUV-exposed areas of the clean glass. When cells were plated on to EDA films which were exposed to patterned DUV irradiation through 40 μm line pair spacings, approximately 90% of the total number of cells plated became preferentially adhered to 40 μm wide lines of unexposed EDA prior to rinsing. However, of the 10% of the total number of cells plated which sedimented onto the 40 μm wide lines of exposed EDA, 78% remained after rinsing. Although the unexposed EDA caused a preferential patterning of the cells, before and after rinsing, the percentage of cells which remained bound to the exposed EDA was four times higher than on exposed EDA which was remodified with UTF-13F.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by letters patent of United States is:

1. A method for preparing a patterned surface for the selective adhesion and outgrowth of cells, comprising:
   (i) coating a substrate with a first compound to obtain an ultra-thin film which is reactive to radiation and has an exposed surface of at least one cell adhesion promoter or cell adhesion inhibitor; and
   (ii) irradiating said ultra-thin film in a pattern to obtain an irradiated film with a surface region in which at least a fraction of said promoter or inhibitor has been removed,
   wherein said cell adhesion promoter contains a group selected from the group consisting of —NHCH$_2$CH$_2$NHCH$_2$CH$_2$NH$_2$, —NHCH$_2$CH$_2$NH$_2$, 11-aminoundecyl, 3-aminopropyl, 3-(-amino-propoxy)- 3,3-dimethyl-1-propenyl, 6-(aminohexyl)propyl, N-(2-aminoethyl)- 3-aminopropyl, —(CH$_2$)$_3$—NH—(CH$_2$)$_2$—NH—(CH$_2$)$_3$, Gly-Arg-Gly-Asp-Tyr-, and Gly-Tyr-Ile-Gly-Ser-Arg-Tyr, and wherein said cell adhesion inhibitor contains a fluorinated alkyl group.

2. The method of claim 1, further comprising:
   (iii) treating the irradiated film with a second compound to bind to said surface region in which at least a fraction of said promoter or inhibitor has been removed.

3. The method of claim 1, wherein said ultra-thin film is coated on a substrate selected from the group consisting of silica, silicon, germanium, gallium, arsenide, epoxy resin, polystyrene, polysulfone, aluminum, platinum, alumina, silicone, fluoropolymers, polyesters, acrylic copolymers, polyglactin, and polylactates.

4. The method of claim 1, wherein said cell adhesion promoter contains a —NHCH$_2$CH$_2$NHCH$_2$CH$_2$NH$_2$ group or a —NHCH$_2$CH$_2$NH$_2$ group.

5. The method of claim 1, wherein said first compound is (a) a cell adhesion promoter compound selected from the group consisting of N-(2-aminoethyl-3-aminopropyl) trimethoxysilane, 11-aminoundecyltrimethoxysilane, 3-aminopropyltrimethoxysilane, 3-aminopropyltriethoxysilane, 3-aminopropylmethyldiethoxysilane, 3-aminopropyldimethylethoxysilane, 3-(1-aminopropoxy)-3,3-dimethyl-1-propenyltrimethoxysilane, 6-(aminohexylaminopropyl)trimethoxysilane, N-(2-aminoethyl)-3-aminopropylmethyldimethoxysilane, bis[3-(trimethoxysilyl)propyl] ethylenediamine, trimethoxysilylpropyldiethylenetriamine, (aminoethylaminomethyl)phenethyltrimethoxysilane, isopropyltri-(n-ethylenediamino)ethyltitanate, neopentyl(diallyl)oxytri(n-ethylenediamino)ethyltitanate, neopentyl(diallyl)oxytri(amino)phenyltitanate, neopentyl(diallyl)oxytri(n-ethylenediamino)ethylzirconate, and neopentyl(diallyl)oxytri(m-amino)phenylzirconate; or (b) a cell adhesion inhibitor compound selected from the group consisting of tridecafluoro-1,1,2,2-tetrahydrooctyl)-1-dimethylchlorosilane, tridecafluoro-1,1,2,2-tetrahydrooctyl)-1-trichlorosilane, tridecafluoro-1,1,2,2-tetrahydrooctyl)-1-methyldichlorosilane, tridecafluoro-1,1,2,2-tetrahydrooctyl)- 1-triethoxysilane, (3,3,3-trifluoropropyl)trichlorosilane, (3,3,3-trifluoropropyl)methyldichlorosilane, (3,3,3-trifluoropropyl)-dimethylchlorosilane, (3,3,3-trifluoropropyl)methyldimethoxysilane, (3,3,3-trifluoropropyl)trimethoxysilane, (heptafluoroisopropoxy) propylmethyldichlorosilane, and (3-pentafluorophenylpropyl) dimethylchlorosilane.

6. A cell-based microsensor, comprising:
   (i) at least one transducer; and
   (ii) a substrate having a patterned surface for the selective adhesion and outgrowth of cells;
   wherein said patterned surface contains at least one region having an exposed surface of at least one cell adhesion promoter, such that said region is spatially related to said transducer so that a cell adhering to said region may be stimulated or detected by said transducer;
   wherein said patterned surface is prepared by a method comprising:
   (i) coating a substrate with a first compound to obtain an ultra-thin film which is reactive to radiation and has an exposed surface of at least one cell adhesion promoter or cell adhesion inhibitor; and
   (ii) irradiating said ultra-thin film in a pattern to obtain an irradiated film with a surface region in which at least a fraction of said promoter or inhibitor has been removed,
   wherein said cell adhesion promoter contains a group selected from the group consisting of —NHCH$_2$CH$_2$NHCH$_2$CH$_2$NH$_2$, —NHCH$_2$CH$_2$NH$_2$, 11-aminoundecyl, 3-aminopropyl, 3-(-aminopropoxy)-3,3-dimethyl-1-propenyl, 6-(aminohexyl)propyl, N-(2-aminoethyl)-3-aminopropyl, —(CH$_2$)$_3$-NH-(CH$_2$)$_2$-NH-(CH$_2$)$_3$, Gly-Arg-Gly-Asp-Tyr-, and Gly-Tyr-Ile-Gly-Ser-Arg-Tyr, and wherein said cell adhesion inhibitor contains a fluorinated alkyl group.

7. The microsensor of claim 6, wherein said method further comprises:
   (iii) treating the irradiated film with a second compound to bind to said surface region in which at least a fraction of said promoter or inhibitor has been removed.

8. The microsensor of claim 6, wherein said ultra-thin film is coated on a substrate selected from the group consisting of silica, silicon, germanium, gallium, arsenide, epoxy resin, polystyrene, polysulfone, aluminum, platinum, alumina, silicone, fluoropolymers, polyesters, acrylic copolymers, polyglactin, and polylactates.

9. The microsensor of claim 6, wherein said cell adhesion promoter contains a —NHCH$_2$CH$_2$NHCH$_2$CH$_2$NH$_2$ group or a —NHCH$_2$CH$_2$NH$_2$ group.

10. The microsensor of claim 6, wherein said first compound is (a) a cell adhesion promoter compound selected from the group consisting of N-(2-aminoethyl-3-aminopropyl) trimethoxysilane, 11-aminoundecyltrimethoxysilane, 3-aminopropyltrimethoxysilane, 3-aminopropyltriethoxysilane, 3-aminopropylmethyldiethoxysilane, 3-aminopropyldimethylethoxysilane, 3-(1-aminopropoxy)-3,3-dimethyl-1-propenyltrimethoxysilane, 6-(aminohexylaminopropyl)trimethoxysilane, N-(2-aminoethyl)-3-aminopropylmethyldimethoxysilane, bis[3-(trimethoxysilyl)propyl] ethylenediamine, trimethoxysilylpropyldiethylenetriamine, (aminoethylaminomethyl)phenethyltrimethoxysilane, isopropyltri-(n-ethylenediamino)ethyltitanate, neopentyl(diallyl)oxytri(n-ethylenediamino)ethyltitanate, neopentyl(diallyl)oxytri(amino)phenyltitanate, neopentyl(diallyl)oxytri(n-ethylenediamino)ethylzirconate, and neopentyl(diallyl)oxytri(m-amino)phenylzirconate; or (b) a cell adhesion inhibitor compound selected from the group consisting of tridecafluoro-1,1,2,2-tetrahydrooctyl)-1-dimethylchlorosilane, tridecafluoro-1,1,2,2-tetrahydrooctyl)- 1-trichlorosilane, tridecafluoro-1,1,2,2-tetrahydrooctyl)-1-methyldichlorosilane, tridecafluoro-1,1,2,2-tetrahydrooctyl)- 1-triethoxysilane, (3,3,3-trifluoropropyl)trichlorosilane, (3,3,3-trifluoropropyl)methyldichlorosilane, (3,3,3-trifluoropropyl)-dimethylchlorosilane, (3,3,3-trifluoropropyl)methyldimethoxysilane, (3,3,3-trifluoropropyl)trimethoxysilane, (heptafluoroisopropoxy) propylmethyldichlorosilane, and (3-pentafluorophenylpropyl) dimethylchlorosilane.

11. An implant, comprising at least one patterned surface for the selective adhesion and outgrowth of cells, wherein said patterned surface is prepared by a method, comprising:

(i) coating a substrate with a first compound to obtain an ultra-thin film which is reactive to radiation and has an exposed surface of at least one cell adhesion promoter or cell adhesion inhibitor; and (ii) irradiating said ultra-thin film in a pattern to obtain an irradiated film with a surface region in which at least a fraction of said promoter or inhibitor has been removed, wherein said cell adhesion promoter contains a group selected from the group consisting of —NHCH$_2$CH$_2$NHCH$_2$CH$_2$NH$_2$, —NHCH$_2$CH$_2$NH$_2$, 11-aminoundecyl, 3-aminopropyl, 3-(-aminopropoxy)-3,3-dimethyl-1-propenyl, 6-(aminohexyl)propyl, N-(2-aminoethyl)-3-aminopropyl, —(CH$_2$)$_3$—NH—(CH$_2$)$_2$—NH—(CH$_2$)$_3$, Gly-Arg-Gly-Asp-Tyr-, and Gly-Tyr-Ile-Gly-Ser-Arg-Tyr, and wherein said cell adhesion inhibitor contains a fluorinated alkyl group.

12. The implant of claim 11, further comprising:

(iii) treating the irradiated film with a second compound to bind to said surface region in which at least a fraction of said promoter or inhibitor has been removed.

13. The implant of claim 11, wherein said ultra-thin film is coated on a substrate selected from the group consisting of silica, silicon, germanium, gallium, arsenide, epoxy resin, polystyrene, polysulfone, aluminum, platinum, alumina, silicone, fluoropolymers, polyesters, acrylic copolymers, polyglactin, and polylactates.

14. The implant of claim 11, wherein said cell adhesion promoter contains a —NHCH$_2$CH$_2$NHCH$_2$CH$_2$NH$_2$ group or a —NHCH$_2$CH$_2$NH$_2$ group.

15. The implant of claim 11, wherein said first compound is (a) cell adhesion promoter compound selected from the group consisting of N-(2-aminoethyl-3-aminopropyl) trimethoxysilane, 11-aminoundecyltrimethoxysilane, 3-aminopropyltrimethoxysilane, 3-aminopropyltriethoxysilane, 3-aminopropylmethyldiethoxysilane, 3-aminopropyldimethylethoxysilane, 3-(1-aminopropoxy)-3,3-dimethyl-1-propenyltrimethoxysilane, 6-(aminohexylaminopropyl)trimethoxysilane, N-(2-aminoethyl)-3-aminopropylmethyldimethoxysilane, bis[3-(trimethoxysilyl)propyl] ethylenediamine, trimethoxysilylpropyldiethylenetriamine, (aminoethylaminomethyl)phenethyltrimethoxysilane, isopropyltri-(n-ethylenediamino)ethyltitanate, neopentyl(diallyl)oxytri(n-ethylenediamino)ethyltitanate, neopentyl(diallyl)oxytri(amino)phenyltitanate, neopentyl(diallyl)oxytri(n-ethylenediamino)ethylzirconate, and neopentyl(diallyl)oxytri(m-amino)phenylzirconate; or (b) a cell adhesion inhibitor compound selected from the group consisting of tridecafluoro-1,1,2,2-tetrahydrooctyl)-1-dimethylchlorosilane, tridecafluoro-1,1,2,2-tetrahydrooctyl)- 1-trichlorosilane, tridecafluoro-1,2,2,2-tetrahydrooctyl)-1-methyldichlorosilane, tridecafluoro-1,1,2,2-tetrahydrooctyl)- 1-triethoxysilane, (3,3,3-trifluoropropyl)trichlorosilane, (3,3,3-trifluoropropyl)methyldichlorosilane, (3,3,3-trifluoropropyl)-dimethylchlorosilane, (3,3,3-trifluoropropyl)methyldimethoxysilane, (3,3,3-trifluoropropyl)trimethoxysilane, (heptafluoroisopropoxy) propylmethyldichlorosilane, and (3-pentafluorophenylpropyl) dimethylchlorosilane.

16. The implant of claim 11, which is in the form of a tube, wherein the inner surface of said tube is said patterned surface.

17. The implant of claim 11, which is in the form of a rolled sheet, wherein at least one side of said sheet is said patterned surface.

18. The implant of claim 11, which is in the form of a transducer.

19. A method for culturing cells, comprising plating cells on a patterned surface for the selective adhesion and outgrowth of cells, wherein said patterned surface is prepared by a process comprising:

(i) coating a substrate with a first compound to obtain an ultra-thin film which is reactive to radiation and has an exposed surface of at least one cell adhesion promoter or cell adhesion inhibitor; and (ii) irradiating said ultra-thin film in a pattern to obtain an irradiated film with a surface region in which at least a fraction of said promoter or inhibitor has been removed, wherein said cell adhesion promoter contains a group selected from the group consisting of —NHCH$_2$CH$_2$NHCH$_2$CH$_2$NH$_2$, —NHCH$_2$CH$_2$NH$_2$, 11-aminoundecyl, 3-aminopropyl, 3-(-aminopropoxy)-3,3-dimethyl-1-propenyl, 6-(aminohexyl)propyl, N-(2-aminoethyl)- 3-aminopropyl, —(CH$_2$)$_3$—NH—(CH$_2$)$_2$—NH—(CH$_2$)$_3$, Gly-Arg-Gly-Asp-Tyr-, and Gly-Tyr-Ile-Gly-Ser-Arg-Tyr, and wherein said cell adhesion inhibitor contains a fluorinated alkyl group.

20. The method of claim 19 wherein said process for preparing said patterned surface further comprises:

(iii) treating the irradiated film with a second compound to bind to said surface region in which at least a fraction of said promoter or inhibitor has been removed.

21. The method of claim 19, wherein said ultra-thin film is coated on a substrate selected from the group consisting of silica, silicon, germanium, gallium, arsenide, epoxy resin, polystyrene, polysulfone, aluminum, platinum, alumina, silicone, fluoropolymers, polyesters, acrylic copolymers, polyglactin, and polylactates.

22. The method of claim 19, wherein said cell adhesion promoter contains a —NHCH$_2$CH$_2$NHCH$_2$CH$_2$NH$_2$ group or a —NHCH$_2$CH$_2$NH$_2$ group.

23. The method of claim 19, wherein said first compound is (a) a cell adhesion promoter compound selected from the group consisting of N-(2-aminoethyl-3-aminopropyl) trimethoxysilane, 11-aminoundecyltrimethoxysilane, 3-aminopropyltrimethoxysilane, 3-aminopropyltriethoxysilane, 3-aminopropylmethyldiethoxysilane, 3-aminopropyldimethylethoxysilane, 3-(1-aminopropoxy)-3,3-dimethyl-1-propenyltrimethoxysilane, 6-(aminohexylaminopropyl)trimethoxysilane, N-(2-aminoethyl)-3-aminopropylmethyldimethoxysilane, bis[3-(trimethoxysilyl)propyl] ethylenediamine, trimethoxysilylpropyldiethylenetriamine, (aminoethylaminomethyl)phenethyltrimethoxysilane, isopropyltri-(n-ethylenediamino)ethyltitanate, neopentyl(diallyl)oxytri(n-ethylenediamino)ethyltitanate, neopentyl(diallyl)oxytri(amino)phenyltitanate, neopentyl(diallyl)oxytri(n-ethylenediamino)ethylzirconate, and neopentyl(diallyl)oxytri(m-amino)phenylzirconate; or (b) a cell adhesion inhibitor compound selected from the group consisting of tridecafluoro-1,1,2,2-tetrahydrooctyl)-1-dimethylchlorosilane, tridecafluoro-1,1,2,2-tetrahydrooctyl)- 1-trichlorosilane, tridecafluoro-1,1,2,2-tetrahydrooctyl)-1-methyldichlorosilane, tridecafluoro-1,1,2,2-tetrahydrooctyl)- 1-triethoxysilane, (3,3,3-trifluoropropyl)trichlorosilane, (3,3,3-trifluoropropyl)methyldichlorosilane, (3,3,3-trifluoropropyl)-dimethylchlorosilane, (3,3,3-trifluoropropyl)methyldimethoxysilane, (3,3,3-trifluoropropyl)trimethoxysilane, (heptafluoroisopropoxy) propylmethyldichlorosilane, and (3-pentafluorophenylpropyl) dimethylchlorosilane.

* * * * *